United States Patent [19]
Weigl et al.

[11] Patent Number: 6,091,502
[45] Date of Patent: Jul. 18, 2000

[54] DEVICE AND METHOD FOR PERFORMING SPECTRAL MEASUREMENTS IN FLOW CELLS WITH SPATIAL RESOLUTION

[75] Inventors: Bernhard H. Weigl; Eric Altendorf, both of Seattle, Wash.

[73] Assignee: Micronics, Inc., Redmond, Wash.

[21] Appl. No.: 09/219,677

[22] Filed: Dec. 23, 1998

[51] Int. Cl.[7] .................................................. G01N 21/25
[52] U.S. Cl. ........................ 356/416; 356/418; 356/419
[58] Field of Search .................................... 356/416, 418, 356/419, 326, 244; 349/62

[56] References Cited

U.S. PATENT DOCUMENTS

| | | | |
|---|---|---|---|
| 5,737,076 | 4/1998 | Glaus et al. | 356/310 |
| 5,920,393 | 7/1999 | Kaplan | 356/364 |
| 5,940,182 | 8/1999 | Lepper, Jr. | 356/416 |

*Primary Examiner*—Frank G. Font
*Assistant Examiner*—Layla Lauchman
*Attorney, Agent, or Firm*—Jerrold J. Litzinger

[57] ABSTRACT

A device and method for performing spectral measurements in flow cells with spatial resolution using a variable transmission optical filter having at least two areas with different optical properties. Light from a light source passes through the variable transmission filter to a flow cell containing a sample to be analyzed. The resultant light pattern is sensed by a detecting means, which analyzes the spectral properties of the sample within the flow cell.

23 Claims, 3 Drawing Sheets

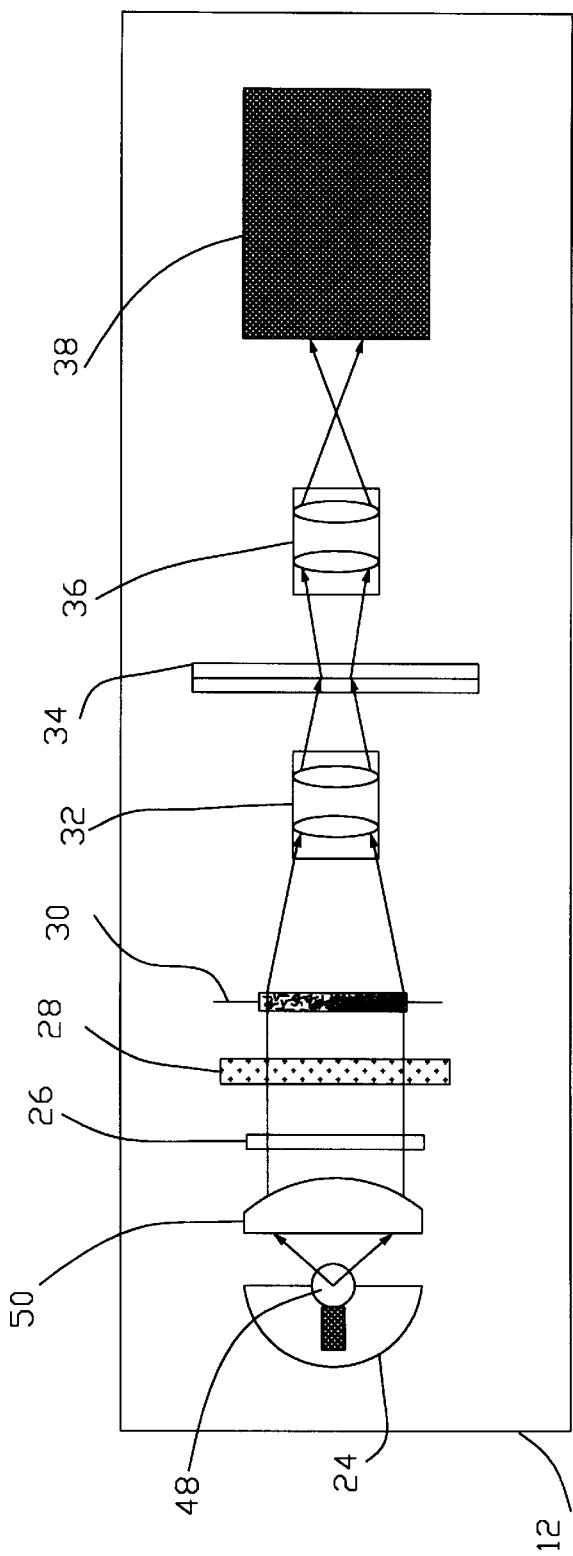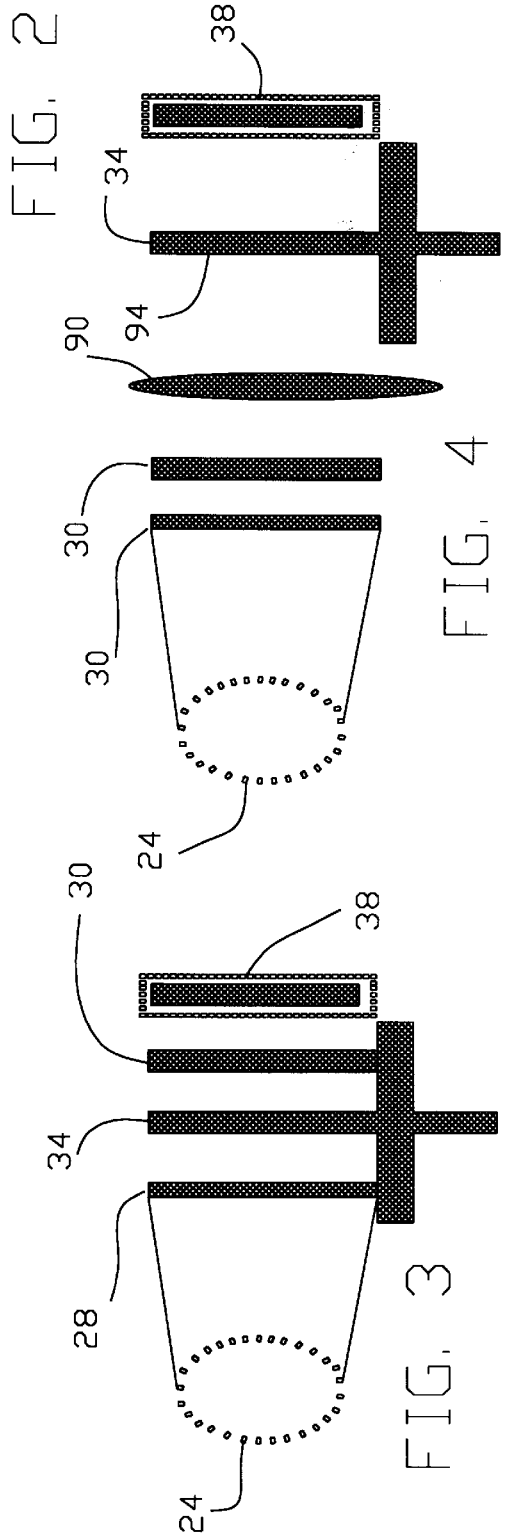

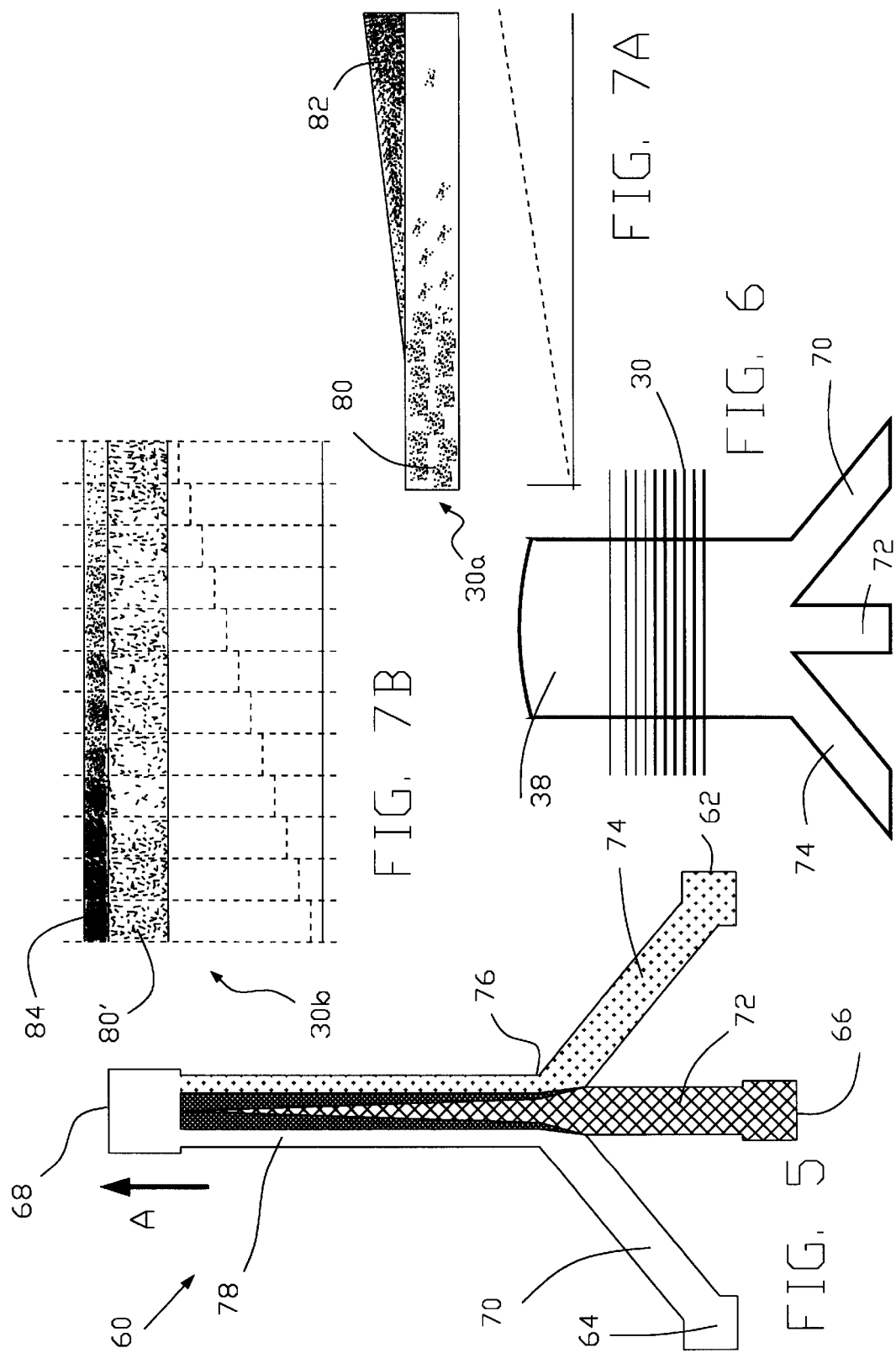

DEVICE AND METHOD FOR PERFORMING SPECTRAL MEASUREMENTS IN FLOW CELLS WITH SPATIAL RESOLUTION

BACKGROUND OF THE INVENTION

1. Field of the Invention

This invention relates generally to optical detection devices, and, in particular, to a device and method for performing spectral measurements in flow cells with spatial resolution.

2. Description of the Related Art

Microfluidic devices have recently become popular for performing analytical testing. Using tools developed by the semiconductor industry to miniaturize electronics, it has become possible to fabricate intricate fluid systems which can be inexpensively mass produced. Systems have been developed to perform a variety of analytical techniques for the acquisition of information for the medical field.

A process called "field-flow fractionation" (FFF) has been developed to separate and analyze micromolecules and particles for analysis by the use of a force applied across a flow channel carrying a variety of particle sizes. Examples of this method are taught in U.S. Pat. Nos. 3,449,938; 4,147,621; 4,214,981; 4,830,756; and 5,156,039.

A related method for particle fractionation is the "Split Flow Thin Cell" (SPLITT) process. this process has been used to develop devices having mesoscale functional element capable of rapid, automated analyses of preselected molecular or cellular analytes in a range of biological and other applications. Examples of this method are taught in U.S. Pat. Nos. 5,296,375; 5,304,487; 5,486,335; and 5,498,392.

Still another method used for assaying fluids involves application of electrical fields to a microfluidic system for providing capillary electrophoresis to separate materials in a flow channel. Examples of this process are taught in U.S. Pat. Nos. 5,699,157; 5,779,868; and 5,800,690.

U.S. Pat. No. 5,716,852 teaches yet another method for analyzing the presence and concentration of small particles in a flow cell using diffusion principles. This patent, the disclosure of which is incorporated herein by reference, discloses a channel cell system for detecting the presence of analyte particles in a sample stream using a laminar flow channel having at least two inlet means which provide an indicator stream and a sample stream, where the laminar flow channel has a depth sufficiently small to allow laminar flow of the streams and length sufficient to allow diffusion of particles of the analyte into the indicator stream to form a detection area, and having an outlet out of the channel to form a single mixed stream. This device, which is known as a T-Sensor, contains an external detecting means for detecting changes in the indicator stream. This detecting means may be provided by any means known in the art, including optical means such as optical spectroscopy, or absorption spectroscopy or fluorescence.

In a paper entitled "An Argument for a Filter Array vs. Linear Variable Filter in Precision Analytical Instrument Applications", the author discusses the advantages and disadvantages of several different types of optical filtering devices which can be employed in conjunction with a detector to enhance the effectiveness of the analytic equipment. The first type of filter described is a filter array (FA) which is composed of discrete segments each having a different bandpass and a uniform passband across each segment. This array is formed by cutting a finished filter into strips and assembling them into an array.

Another type of filter described is a linear variable filter (LVF). This filter is constructed by varying the thickness of the thin films which define the spectral characteristics. The wavelength changes as a function of thickness, creating a continuously variable passband along the length of the filter, with every segment, no matter how small, having a different passband.

One way to look at these filters is to think of the LVF as an analog device and the FA as a digital device, with each having certain advantages and disadvantages. For example, the LVF has the advantage that, regardless of the size and number of pixels behind the filter, each sees a different segment of the spectrum. The number of channels is limited only by the number of pixels and available energy. However, as the width of one segment of the LVF increases, the resolution decreases because each portion of the segment has a different passband. In addition, because it is the change in layer thickness of the given materials which determines the passband variance, the spectral region over which a single LVF can perform is limited by the properties of a set of coating materials, and the change in passband characteristics is determined by the coating design.

Advantages of the FA include: the spectral region can be very broad, as each segment can be made with different coating materials, making it possible to take advantage of the absorption characteristics of materials to achieve a very high rejection outside the passband; any segment can have spatial and optical characteristics totally independent of the other segments of the filter, and the elements can also be made in different widths, thus allowing wider segments in regions of lower sensitivity.

It would be desirable, particularly in the field of microfluidic flow analysis, to produce a filter which would allow variable transmission in any direction or geometry (e.g., a two-dimensional matrix which is variable in one dimension, and having variable optical density in the other dimension for the low-cost spectral analysis of a sample over an extremely wide dynamic range). This could be accomplished by a filter upon which, by microlithographic or printing techniques, various absorbing material is deposited or removed to form the desired absorption pattern. In its simplest form, the technique would involve loading an ink-jet type printer with an assortment of well-defined optically absorbing dyes, and printing the desired structures on a sheet of transparent material. Such a technique would permit the production of filters with variable transmission in any orientation and geometry.

The aforementioned T-Sensor device allows the fluorescence and absorption detection of analytes in complex samples based on diffusion separation in layers of laminar flows. By imaging an area of the T-Sensor, the fluorescence or absorption of so-called diffusion interaction zones between a sample, a detection, and a reference stream can be determined. The intensity of these diffusion interaction zones is then used to determine the analyte concentration. By placing a linear variable filter or a filter array in the optical path such that the transmission variation of the filter occurs in the flow direction, it is possible to spectroscopically determine absorption or fluorescence in a T-Sensor. A detecting means, such as a charge-coupled display (CCD) device, can then be positioned such that it will see slices of very similar cross sections of the T-Sensor channel, each measured at a different wavelength. Many analytic parameters can be derived from these cross section profiles, including reference background intensity and profile shape; reference interaction zone intensity, width, and shape of both dye and reference diffusion profile; detection solution background intensity and profile shape; sample interaction zone intensity, width, shape, of both dye and same diffusion profile; sample background intensity and profile shape; x-location of reference interaction maximum intensity; and x-location of sample interaction maximum intensity.

SUMMARY OF THE INVENTION

Accordingly, it is an object of the present invention to provide a device which can be used to measure a variety of analytes which are determined using a variety of detection wavelengths.

It is a further object of the present invention to provide a device which can simultaneously detect several analytes with different absorption/fluorescence characteristics within the same flow cell.

It is still a further object of the present invention to provide a device in which spectroscopic measurements with spatial resolution may be taken in real time, without having to mechanically move gratings, filter wheels, or other optical components.

These and other objects and advantages of the present invention will be readily apparent in the description that follows.

BRIEF DESCRIPTION OF THE DRAWINGS

FIG. 2 is a more detailed diagram of the optical detector section of the system of FIG. 1;

FIG. 3 is a view similar to FIG. 2 depicting an alternative embodiment of the present invention;

FIG. 4 is a view similar to FIG. 2 depicting another alternative of the present invention;

FIG. 5 is a graphic representation of a T-Sensor for use with the present invention;

FIG. 6 is a graphic representation of the T-Sensor of FIG. 6 showing a filter array projected onto its plane; and FIGS. 7A and 7B show several examples of filter arrays constructed according to the present invention.

DETAILED DESCRIPTION OF THE PREFERRED EMBODIMENTS

Figure 1:
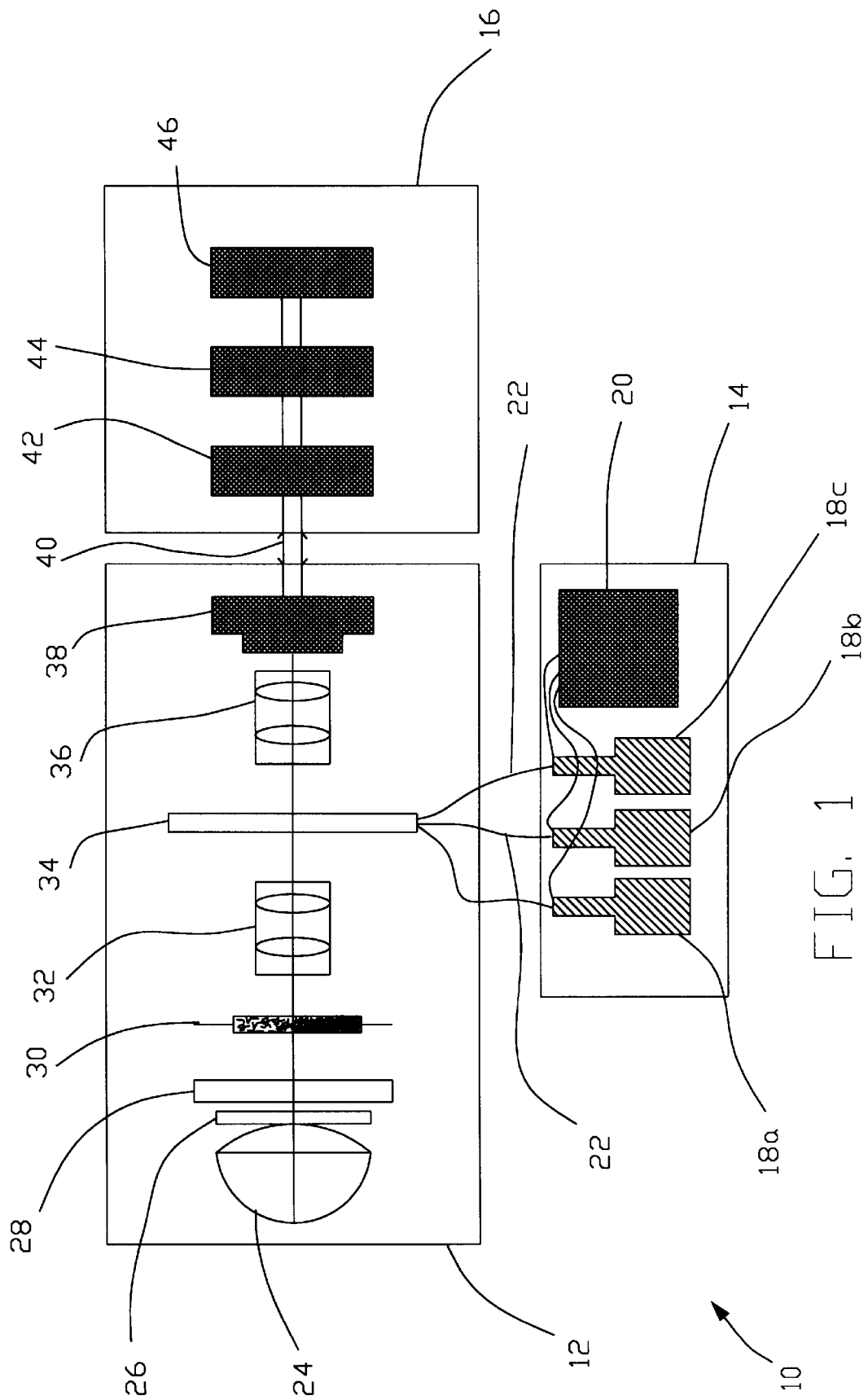
FIG. 1 is a representative block diagram of a microfluidic system employing the present invention.

Referring now to the drawings, a microfluidic system, generally designated at 10, which embodies the principles of the present invention is shown.

System 10 consists of an optical module 12, a fluid module 14, and a data processing module 16. Fluid module 14 contains a pump assembly 18 having a plurality of pumps 18a, 18b, 18c, and also a reagent unit 20. Unit 20 preferably contains a plurality of different fluids which may be joined with a sample fluid in question to and in the analysis of the sample. Representative reagents include dilutents, lysing agents, indicator dyes, fluorescent compounds, fluorescent beads, and reporter beads for flow cytometric measurement.

Fluid module 14 is coupled to optical module 12 via a plurality of connecting hoses 22. Optical module 12 consists of a light source assembly 24, a first filter 26, a diffuser plate 28, a variable transmission filter 30, a projection optic unit 32, a liquid analysis cartridge 34, a collection optic unit 36 and a detector assembly 38. Hoses 22 from fluid module 14 are connected directly to cartridge 34 within optical module 12. Hoses 22 deliver the sample fluid, along with the necessary reagents from unit 20 to perform a particular analysis, to cartridge 34, Cartridge 34 preferably carries at least one flow cell having the geometry for detection of specific attributes of the sample fluid to be analyzed. The term flow cell refers to any kind of channel having an optically observable region to monitor an optical property of a flowing or still liquid or gas. U.S. patent application Ser. No. 09/080,691, which was filed on May 18, 1998, the disclosure of which is incorporated herein by reference, describes one embodiment of an analysis cartridge suitable for use with the present invention.

The output of optical module 12 is transmitted to data processing module 16 by a coupling means 40, allowing information from module 12 to be processed and analyzed at module 16. Module 16 includes a processing electronics unit 42, a data processing software unit 44, and a display readout 46.

Having generally described the elements of the device of the present invention, a more detailed description of the operation of the optical module of a microfluidic system which embodies the present invention will now be described. Referring now to FIG. 2, light source assembly 24 includes a light source 48 and a condenser lens 50. Light source 48, which is a quartz halogen bulb in the present embodiment, preferably exhibits uniform light distribution over the imaged area; however, the only requirement from light source 48 is to provide constant light distribution over the area. Lens 50 acts to collimate the light generated from source 48. Light source 48 may also consist of an electroluminescent foil.

As light from source 48 passes through lens 50, it is transmitted through filter 26 to filter out the infrared band to reduce heat, and then through diffuser plate 28 which provides uniform light distribution. Light exiting diffuser plate 28 projects upon variable transmission filter array 30, which passes the desired optical pattern to projection optic unit 32. Unit 32 then projects the image of filter array 30 onto liquid analysis cartridge 34. Collection unit 36 senses the light on the other side of cartridge 34 and send this information to detector assembly 38. Detector 38 is preferably a CCD camera in the present embodiment.

In the present embodiment, the analysis of the sample within cartridge 30 takes place within a T-Sensor of the type which is shown and described in U.S. Pat. No. 5,716,852. FIGS. 5 and 6 show several representations of a T-Sensor used in the present invention. Referring now to FIG. 5, a T-Sensor 60 is shown, having a sample stream inlet 62, a reference stream solution inlet 64, a center detection stream inlet 66, and an exit port 68. In operation, a reference solution 70, which contains a known concentration of an analyte, enters sensor 60 via inlet 64, a detection solution 72, which contains detection reagents (such as a fluorescent indicator), enters via center inlet 66, and a sample stream 74, which contains an unknown sample solution containing a mixture of soluble and insoluble particles, enters via inlet 62. All streams flow adjacent one another in the direction of arrow A after merging at a junction 76 of a central detection channel 78, which terminates at exit port 68.

As a result of the characteristics of sensor 60, particles diffuse from solutions 70 and 74 into solution 72 and react with solution 72, forming diffusion interaction zones between the fluid layers. If an indicator solution is used in detection solution 72, the diffusion interaction zones will be optically detectable, with the optical signal being a function of concentration of the analyte.

FIG. 6 shows a representation of T-Sensor 60 with filter array 30 projected onto the plane of the detection channel; the spatial properties of the fluid layers in the detection channel can now be determined while retaining all cross-channel spatial information such as positions and intensities of the diffusion interaction zones.

Several examples of variable transmission filter array 30 are shown in FIGS. 7A and 7B. Filter 30a, seen in FIG. 7A, is composed of a substrate 80 which is coated with a film 82 having a continuously variable thickness. As can be seen in the graph of FIG. 7A, the maximum transmission wavelength of filter 30a varies linearly across its length as a function of the thickness of film 82. Filter 30b of FIG. 7B is composed of a substrate 80' upon which a series of parallel filter strips 84, each having a different transmission characteristic, are glued or otherwise affixed. The graph of FIG. 7B indicates that the transmission wavelength varies in discrete stages across the length of filter 30b.

Each of these filters have certain desirable qualities: filter 30a is generally less expensive to manufacture, and allows greater flexibility in the types of sequences of filters, while filter 30b, which contains no discrete bandpass windows, allows for higher wavelength resolution. The appropriate filter can be selected to meet the requirements of the particular analysis desired.

Many combinations of variable transmission filters, optical elements and flow cells can be used to achieve the desired analytical information. Such filters can consist of zones of various long pass, short pass, neutral density, polarizing, bandpass and many other types of filters or combinations thereof, or can consist of layers of filters on top of each other (e.g., an array of bandpass filters on top of an array of long pass filters for the reduction of stray light in fluorescence measurements). In many cases, filters would be used not only on the light source side of the flow cell to generate, for example, bands of monochromatic light, but also on the detector side of the flow cell, either in close proximity of the plane of the flow cell, or coupled to the spatial detector array (e.g., fluorescence emission spectroscopy).

FIGS. 3 and 4 show several alternative arrangements of the elements of the present invention in a microfluidic system. Referring now to FIG. 3, variable transmission filter 30 is placed on the opposite side of cartridge 34 from light source 48, between cartridge 34 and CCD camera 38.

FIG. 4 shows another embodiment for the elements of the present invention. In FIG. 4, filter 30 is placed between light source 24 and an imaging optics unit 90 which projects the image of filter 30 into the plane of the flow cell within cartridge 34, as shown at 94. It has been determined that the device of FIG. 4 has been useful when performing fluorescence or absorption measurements.

Other types of filters can conceivably be used to perform spectroscopic measurements with a spatial detector array using the principles of the present invention. For example, a two-dimensional variable filter, consisting of a matrix of filter squares or rectangles to generate a filter with variable properties along both the length and width of the filter, is possible. Such a filter would not retain spatial resolution of the flow cell, but it would allow the device to measure several optical properties simultaneously. For example, such an array could have transmission windows of increasing wavelength in one dimension, and increasing optical densities in the other dimension. This would allow for determination of the absorption maximum of liquid over a large dynamic range.

Another type of filter which may be used in the present invention uses a programmable liquid crystal display (LCD) screen. In this filter, the LCD screen, which can either transmit light or reflect light according to the requirements of the system, acts as the variable transmission filter. The individual pixels of the LCD screen are programmed as either light or dark (black or white) using a mircroprocessor device to generate variable patterns on the screen. The light from the light source is then transmitted (or reflected) to the flow cell containing the sample within the cartridge, and is sensed by the detecting means to analyze the properties of the sample to be tested.

While the present invention has been shown and described in terms of a preferred embodiment thereof, it will be understood that this invention is not limited to this particular embodiment and that many changes and modifications may be made without deporting from the true spirit and scope of the invention as defined in the appended claims.

What is claimed is:

1. A device for analyzing the spectral properties of a sample, comprising:
   a light source;
   a microfluidic channel for holding a flowing sample to be analyzed;
   a variable transmission optical filter having at least two areas with different optical properties;
   and detecting means capable of measuring light intensity with at least one dimensional resolution;
   wherein when light from said light source is directed at said flowing sample within said channel and through said optical filter and is received by said detecting means, said detecting means analyzes the spectral properties of the flowing sample.

2. The device of claim 1, wherein said optical filter is positioned between said light source and said channel.

3. The device of claim 1, wherein said optical filter is positioned between said channel and said detecting means.

4. The device of claim 1, wherein said optical filter comprises a linear variable filter.

5. The device of claim 1, wherein said optical filter comprises a filter array.

6. The device of claim 1, wherein said optical filter is comprised of a plurality of bandpass filters.

7. The device of claim 1, wherein said detecting means includes a CCD camera.

8. The device of claim 1, further comprising a second variable transmission optical filter having at least two areas with different optical properties, with said sample containing channel being positioned between said optical filters.

9. The device of claim 1, wherein said optical filter is constructed from a combination of filters selected from a group comprised of bandpass filters, longpass filters, polarizing filters and neutral density filters.

10. The device of claim 1, wherein said optical filter comprises a programmable LCD screen having variable optical transmission.

11. The device of claim 1, wherein said optical filter comprises a programmable LCD screen having variable optical reflection.

12. The device of claim 1, wherein said optical filter comprises a printed filter array.

13. The device of claim 1, wherein said sample holding channel comprises a flow cell.

14. The device of claim 13, wherein said sample holding chamber comprises a plurality of flow cells.

15. The device of claim 1, wherein said optical filter is comprised of at least two areas having different optical properties which are printed onto a substrate by a computer addressable ink jet type printer.

16. A method of analyzing the optical properties of a sample, comprising the steps of:

locating a flowing sample to be analyzed within a microfluidic measurement cell;

directing a light source at said measurement cell;

filtering the light from said light source using a variable transmission optical filter having at least two areas with different optical properties;

receiving the light from said light source which has passed through said optical filter and said flowing sample within said measurement cell at a detection means and analyzing the spectral properties of said sample.

17. The method of claim 16, wherein said optical filter is positioned between said light source and said measurement cell.

18. The method of claim 16, wherein said optical filter is positioned between said measurement cell and said detection means.

19. The method of claim 16, wherein said detection means comprises a CCD camera.

20. A method of making an optical filter, comprising the steps of:

selecting an optically transparent substrate;

and attaching to said substrate at least one optically active substance having at least two areas of different optical properties;

wherein said method of attaching comprises printing said areas of different optical properties with an ink jet printer.

21. The device of claim 1 wherein said microfluidic channel is contained within a T-Sensor.

22. The method of claim 16, wherein said optical filter comprises a linear variable filter.

23. The method of claim 22, wherein said microfluidic measurement cell is positioned within a T-Sensor.

* * * * *